(12) United States Patent
Kawamata et al.

(10) Patent No.: US 8,512,646 B2
(45) Date of Patent: Aug. 20, 2013

(54) DEVICE FOR GENERATING STERILIZING GAS, CATALYST CARTRIDGE APPLIED TO DEVICE FOR GENERATING STERILIZING GAS AND DEVICE FOR PROCESSING FOR STERILIZATION

(75) Inventors: Katsuhiko Kawamata, Matsuyama (JP); Yasushi Suzuki, Saijo (JP); Shunsuke Nishiyama, Matsuyama (JP); Motoboru Iio, Saijo (JP)

(73) Assignees: Wiz Systems Corporation, Ehime (JP); Seavile Inc., Ehime (JP); Hoei Denki Co., Ltd., Osaka (JP)

( * ) Notice: Subject to any disclaimer, the term of this patent is extended or adjusted under 35 U.S.C. 154(b) by 161 days.

(21) Appl. No.: 13/061,137

(22) PCT Filed: Aug. 27, 2009

(86) PCT No.: PCT/JP2009/064985
§ 371 (c)(1),
(2), (4) Date: Apr. 26, 2011

(87) PCT Pub. No.: WO2010/024345
PCT Pub. Date: Mar. 4, 2010

(65) Prior Publication Data
US 2011/0189058 A1    Aug. 4, 2011

(30) Foreign Application Priority Data

Aug. 29, 2008  (JP) ................ P2008-221628

(51) Int. Cl.
*B01J 8/02* (2006.01)
*B01J 35/02* (2006.01)

(52) U.S. Cl.
USPC ........... 422/222; 422/211; 422/27; 422/28; 422/29; 422/198

(58) Field of Classification Search
USPC ............... 422/27, 28, 29, 211, 222, 198
See application file for complete search history.

(56) References Cited

U.S. PATENT DOCUMENTS
4,407,785 A * 10/1983 Pfefferle ............... 423/659

FOREIGN PATENT DOCUMENTS
| JP | 4936594 A | 4/1974 |
| JP | 2180642 A | 7/1990 |
| JP | 2253825 A | 10/1990 |
| JP | 6154622 A | 6/1994 |
| JP | 2005143580 A | 6/2005 |

OTHER PUBLICATIONS
Machine translation of JP 2005-143580 A.*

* cited by examiner

*Primary Examiner* — Jill Warden
*Assistant Examiner* — Lessanework Seifu
(74) *Attorney, Agent, or Firm* — Haverstock & Owens LLP

(57) ABSTRACT

A device for generating a sterilizing gas includes a methanol gas generation device (11) for vaporizing methanol to generate a methanol gas, a tubular part (12) and a catalyst section (13). The tubular section (12) is arranged on top of the methanol gas generation device (11) to provide a flow path for upwardly directing the methanol gas generated by the methanol gas generation device by natural convection. The tubular section also operates to mix the methanol gas with a predetermined proportion of air. The catalyst section (13) is arranged on top of the tubular section (12) for turning the methanol gas mixed with the air at the predetermined proportion in the tubular section (12) into radicals by a catalyzed reaction. The catalyst section (13) is formed by a turn-into-radical reaction catalyst layer (30) obtained on forming a thin metal sheet (35a) to a honeycomb structure.

8 Claims, 13 Drawing Sheets air, 5 liters; methanol, 3cc shown enlarged 35a
35b

US 8,512,646 B2

DEVICE FOR GENERATING STERILIZING GAS, CATALYST CARTRIDGE APPLIED TO DEVICE FOR GENERATING STERILIZING GAS AND DEVICE FOR PROCESSING FOR STERILIZATION

TECHNICAL FIELD

This invention relates to a device for generating a sterilizing gas that sterilizes an object by a methanol radical gas, exhibiting the properties as radicals, and that is generated from methanol by a catalyzed reaction. The methanol radical gas is referred to below as an MR gas. This invention also relates to a catalyst cartridge exchangeably mounted on the device for generating a sterilizing gas, and to a device for sterilization.

The present Application for patent claims priority rights based on Japanese Patent Application 2008-221628, filed in Japan on Aug. 29, 2008. The Patent Application of the senior filing data is to be incorporated by reference into the present Application.

BACKGROUND ART

The sterilization and/or the sterilization system by a gas that exhibits the properties as radicals and that is generated from methanol by a catalyzed reaction (MR gas) represents a new sterilization technology that is able to deactivate even DNA. It is dehydrogenation sterilization different from oxidization sterilization that uses an ethylene oxide gas (EO) or ozone which has so far been predominantly used as a sterilizing gas for therapeutic utensils. The new sterilization technology also has been widely recognized to be free from persistency or corrosion and is attracting attention in many technical fields.

The MR gas means a radical gas that is generated by a catalyzed reaction from methanol and that exhibits strong sterilization performance and/or sterilization effects. It has strong permeation performance and operates even under an atmospheric pressure to disinfect deep into the inside of the object being sterilized. It has many desirable properties, viz., it is non-corrosive to metal, non-aggressive to plastics and non-selective of material types of the object, while it is not persistent on the object being sterilized. In addition, it may be used with advantage as a measure against viruses or DNA contamination, and also has an effect in detoxification (deactivation) of toxic gases. Furthermore, it may be used for sterilization of electrical or electronic equipment or a PC system formed from semiconductors even when the equipment or system is in live state.

In a conventional MR gas sterilization system, methanol stored in a methanol tank is vaporized by a vaporization heater and thereby turned into a methanol gas. The so generated methanol gas is reacted in a catalyst section provided on top of a vaporization heater to generate an MR gas as heat is applied to the catalyst section from a heater. See for example Patent Document 1.

Patent Document 1: Japanese Laid-Open Patent Publication 2005-130993

DISCLOSURE OF THE INVENTION

Problem to be solved by the Invention

The conventional MR gas generation device has a catalyst section as large as 150 to 180 mm in terms of a diametrical size. However, with such catalyst section, it is difficult to maintain a constant temperature necessary for a turn-into-radical reaction of the methanol gas. It has thus been necessary to provide the electrical heater within the bulk of the catalyst to control the temperature by heating from time to time to maintain the temperature necessary for the turn-into-radical reaction.

In such conventional MR gas generation device, temperature variations in the course of the catalyzed reaction are so severe that it has not been possible to generate the MR gas having a constant concentration. On the other hand, it has been necessary to provide a catalyst section as large as 150 to 180 mm as well as the above mentioned electrical heater for heating. The catalyst section is thus necessarily large in size to render it difficult to reduce the size of the MR gas generation device itself in order to enhance its field of application.

The present invention has been completed in view of the above mentioned problems of the related technique. The present invention provides a device for generating a sterilizing gas that is able to maintain a constant catalyzed turn-into-radical reaction temperature (constant self-reaction temperature) to generate a sterilizing gas of the stabilized concentration and that lends itself to device size reduction. Further, the present invention provides a catalyst cartridge used for the device for generating a sterilizing gas, and a device for sterilization.

To solve the above mentioned problems, the present inventors have conducted eager searches from a variety of perspectives and, as a result, found that, by using a catalyst of a honeycomb structure, it is possible to maintain a constant catalyzed turn-into-radical reaction temperature (self-reaction temperature). This finding has led to completion of the present invention.

A device for generating a sterilizing gas according to the present invention comprises a methanol gas generation section for vaporizing methanol to generate a methanol gas, a tubular section and a catalyst section. The methanol gas generation section generates a methanol gas. The tubular section is arranged on top of the methanol gas generation section to provide a flow path for upwardly directing the methanol gas generated by the methanol gas generation device by natural convection. The tubular section also operates to mix the methanol gas with a predetermined proportion of air. The catalyst section is arranged on top of the tubular section for turning the methanol gas mixed with the air at the predetermined proportion in the tubular section into radicals by a catalyzed reaction. The catalyst section is formed by a turn-into-radical reaction catalyst layer obtained on forming a thin metal sheet to a honeycomb structure.

A catalyst cartridge according to an embodiment of the present invention is exchangeably mounted in a device for generating a sterilizing gas. The device for generating a sterilizing gas includes a methanol gas generation section for generating a methanol gas, and a tubular section. The tubular section is arranged on top of the methanol gas generation section to provide a flow path for upwardly directing the methanol gas generated by the methanol gas generation section by natural convection. The tubular section also operates to mix the methanol gas with a predetermined proportion of air. The catalyst cartridge is formed by a turn-into-radical reaction catalyst layer obtained on forming a thin metal sheet to a honeycomb structure. The catalyst cartridge, arranged on top of the tubular section, operates for turning the methanol gas, mixed with a predetermined proportion of air in the tubular section, into radicals by a catalyzed reaction.

A device for processing for sterilization according to an embodiment of the present invention comprises a device for generating a sterilizing gas, which device for generating a sterilizing gas includes a methanol gas generation section for vaporizing methanol to generate a methanol gas, a tubular section and a catalyst section. The tubular section is arranged on top of the methanol gas generation device to provide a flow path for upwardly directing the methanol gas generated by the methanol gas generation section by natural convection. The tubular section also operates to mix the methanol gas with a predetermined proportion of air. The catalyst section is arranged on top of the tubular section for turning the methanol gas mixed with the air at the predetermined proportion in the tubular section into radicals by a catalyzed reaction. The catalyst section is formed by a turn-into-radical reaction catalyst layer obtained on forming a thin metal sheet to a honeycomb structure.

BEST MODE FOR CARRYING OUT THE INVENTION

Figure 1:
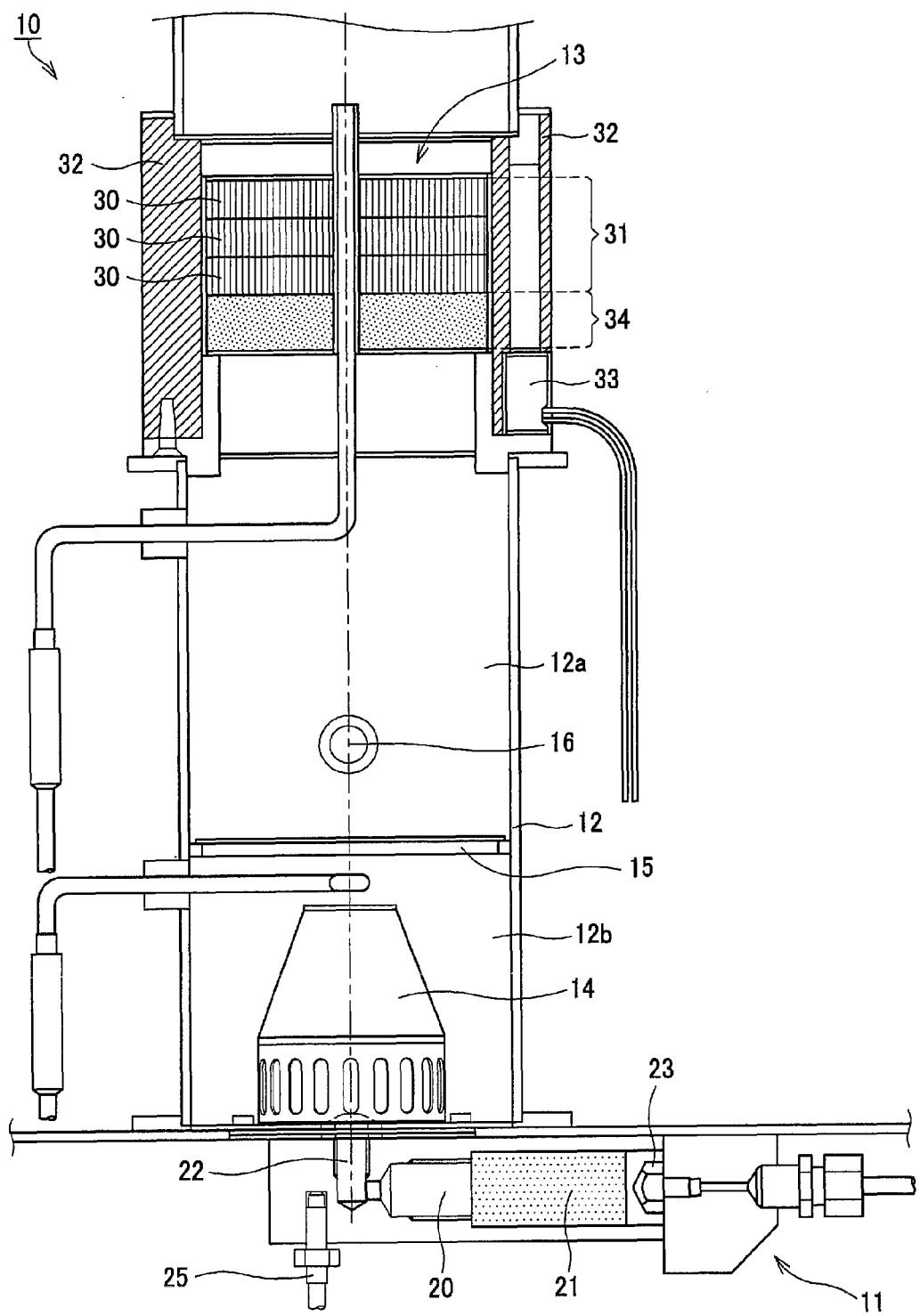
FIG. 1 is a schematic view showing an MR gas generation device.

A sterilizing gas generation device according to the present invention will now be described with reference to an MR gas generation device taken as a specified example. By 'sterilizing' in meant not only the processing for sterilization but also that for bacteria killing or bacteria elimination, decontamination and DNA deactivation. In each figure, the same reference numerals are used to depict the same component parts.

FIG. 1 schematically shows an MR gas generation device according to the present embodiment. Referring to FIG. 1, an MR gas generation device 10 of the present embodiment includes a methanol gas generation unit 11, a tubular section 12 and a catalyst cartridge 13. Methanol is supplied from a methanol tank, not shown, to the MR gas generation device 10 where methanol is vaporized to yield the methanol gas. The tubular section 12 is provided on the top of the methanol gas generation unit 11 to permit the methanol gas generated by the methanol gas generation unit 11 to be mixed with air as well as to cause the methanol gas generated to flow upwards by natural convection. The catalyst cartridge 13 is provided in contiguity to the tubular section 12 so as to be dismounted as desired on top of a flow path of the methanol gas to turn the methanol gas into radicals by a catalyzed reaction to generate an MR gas. The operation of respective components will now be explained in detail.

Initially, the methanol gas generation unit 11 composing the MR gas generation device 10 will be explained. The methanol gas generation unit 11 vaporizes methanol to generate the methanol gas which is a reaction product of the turn-into-radical reaction. The so generated methanol gas is delivered to the tubular section 12.

Figure 2:
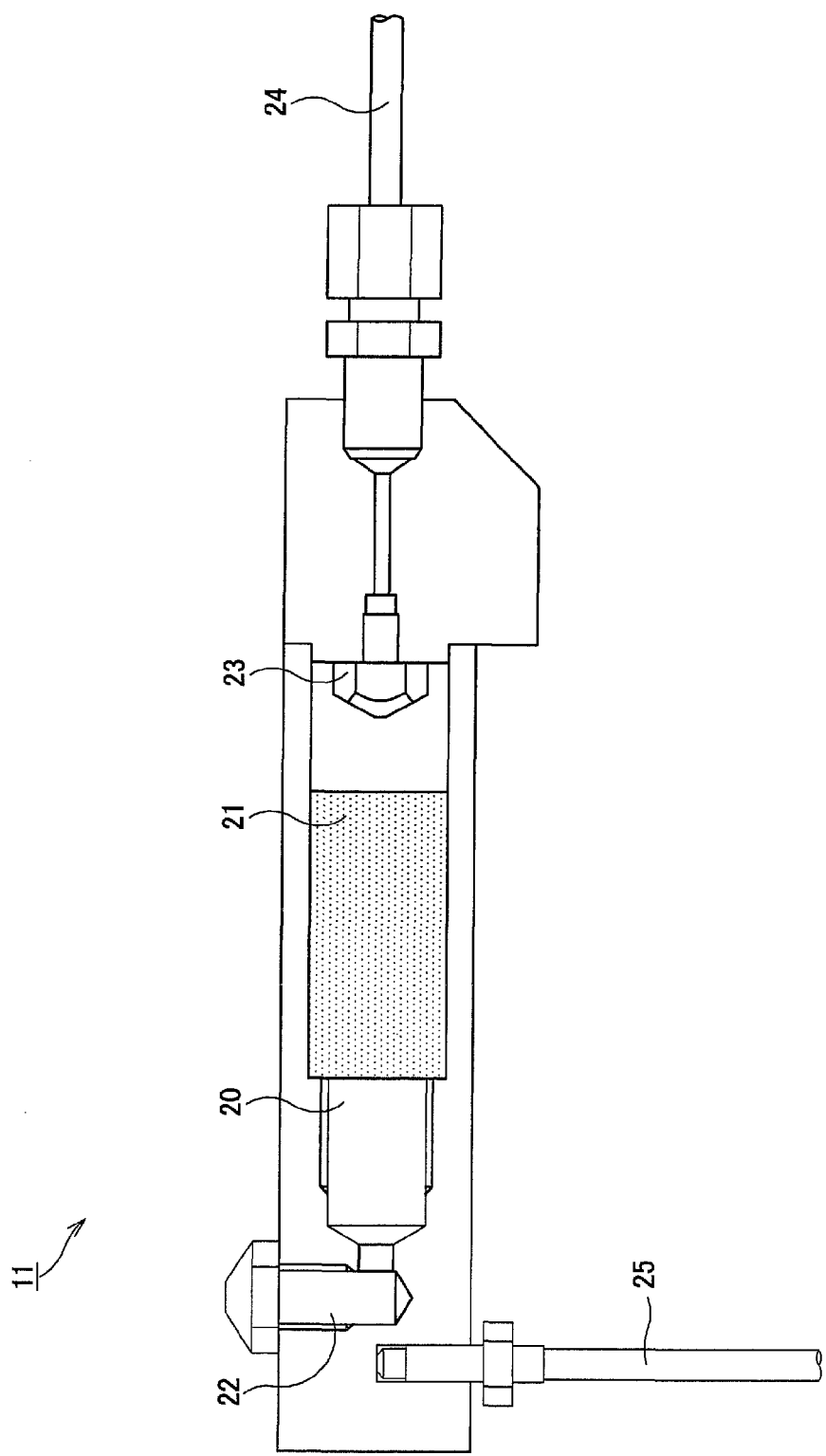
FIG. 2 is a schematic view showing a methanol gas generation device that composes an MR gas generation device.

FIG. 2 depicts a schematic view of the methanol gas generation unit 11. Referring to FIG. 2, a methanol tank, not shown, holding methanol as a feedstock material, is connected to the methanol gas generation unit 11. The methanol gas generation unit includes at least an electrical heater 20, a thermal medium 21, a vaporizing nozzle 22 and an additional nozzle 23. The electrical heater 20 vaporizes methanol by heating, and the thermal medium 21, formed of temperature stabilizing metal, such as sintered metal, controls the temperature in vaporizing methanol supplied from the methanol tank. The vaporizing nozzle 22 guides the vaporized methanol to an upper portion within the MR gas generation device 10. The additional nozzle 23 is used for spraying the methanol, delivered from the methanol tank, in the form of a mist, which is then caused to flow towards the thermal medium 21.

In the methanol gas generation unit 11, the methanol delivered from the methanol tank is heated by the electrical heater 20, under temperature control by the thermal medium 20, so as to be vaporized to form a methanol gas. The so generated methanol gas is passed through a vaporizing cover 14 to flow towards an upper portion of the MR gas generation device 10, that is, towards the catalyst cartridge 13, under the effect of natural convection.

This process is now explained in more detail. As the electrical current begins to be supplied to the electrical heater 20, the thermal medium 21, passed through by the methanol delivered from the methanol tank via a communication vessel 24 for methanol conduction, begins to be heated to 120 to 130° C. under the heat from the electrical heater 20. As the methanol, delivered from the methanol tank, travels through the thermal medium 21, it is heated by heat evolved in the thermal medium and vaporized to generate the methanol gas. The so generated methanol gas is diffused as it travels through the vaporizing nozzle 22 and the vaporizing cover 14 to flow towards the catalyst cartridge 13 through the tubular section 12 under the effect of natural convection.

There is no particular limitation to the thermal medium 21 formed of temperature stabilizing metal, such as sintered metal, used for the methanol gas generation unit 11, and any of a large variety of materials may be used for the thermal medium. A metal material in the form of a thin wire, used for a metal brush, may be used only by way of an example.

Specifically, such a metal material that is hardly oxidized and that is capable of maintaining a constant temperature is preferentially be used. As will be explained later in detail, any variations in temperature in the methanol gas generation unit 11 significantly affect the catalyst reaction temperature in the catalyst cartridge 13 to destabilize the catalyst reaction temperature. Hence, the thermal medium 21 is formed of a metal material capable of maintaining a constant temperature, whereby temperature variations in the catalyst cartridge 13 may be suppressed to provide for a stabilized catalyst reaction temperature in the catalyst cartridge 13. For example, the thermal medium 21, formed of stainless steel, such as stainless steel species SUS304, may preferably be used.

The main portions of the methanol gas generation unit 11 are also preferably formed of a metal material that is hardly oxidized and that has the property of maintaining a constant temperature. For example, the above mentioned SUS304 stainless steel species is most preferred. By forming the methanol gas generation unit 11 from such metal material, heat may be uniformly transmitted to methanol delivered from the methanol tank. It is thus possible to vaporize methanol under temperature control to 120 to 130° C. with fluctuations of ca. ±0.5° C. In using stainless steel, not only the stainless steel species SUS304 but also stainless steel species SUS303 or SUS316 may be used without limitations.

The methanol gas generation unit 11 includes the additional nozzle 23 by means of which methanol, supplied from the methanol tank through a methanol supplying communication tube 24, is turned into a mist by e.g., a pump, and the so formed mist of methanol may then be sprayed onto the thermal medium 21. By spraying the methanol in the form of the mist from the methanol tank via the nozzle 23 and heating the methanol in the form of the mist via the electrical heater 20 and the thermal medium 20, it is possible to vaporize methanol in stability as a constant temperature is maintained.

Since the methanol gas is generated in this manner under a stabilized state of a constant temperature, it is possible to suppress temperature variations in the methanol gas generation unit 11 to suppress temperature variations in the catalyzed reaction in the catalyst cartridge 13 more effectively as later explained. In this manner, the MR gas may be generated in stability.

Figure 3:
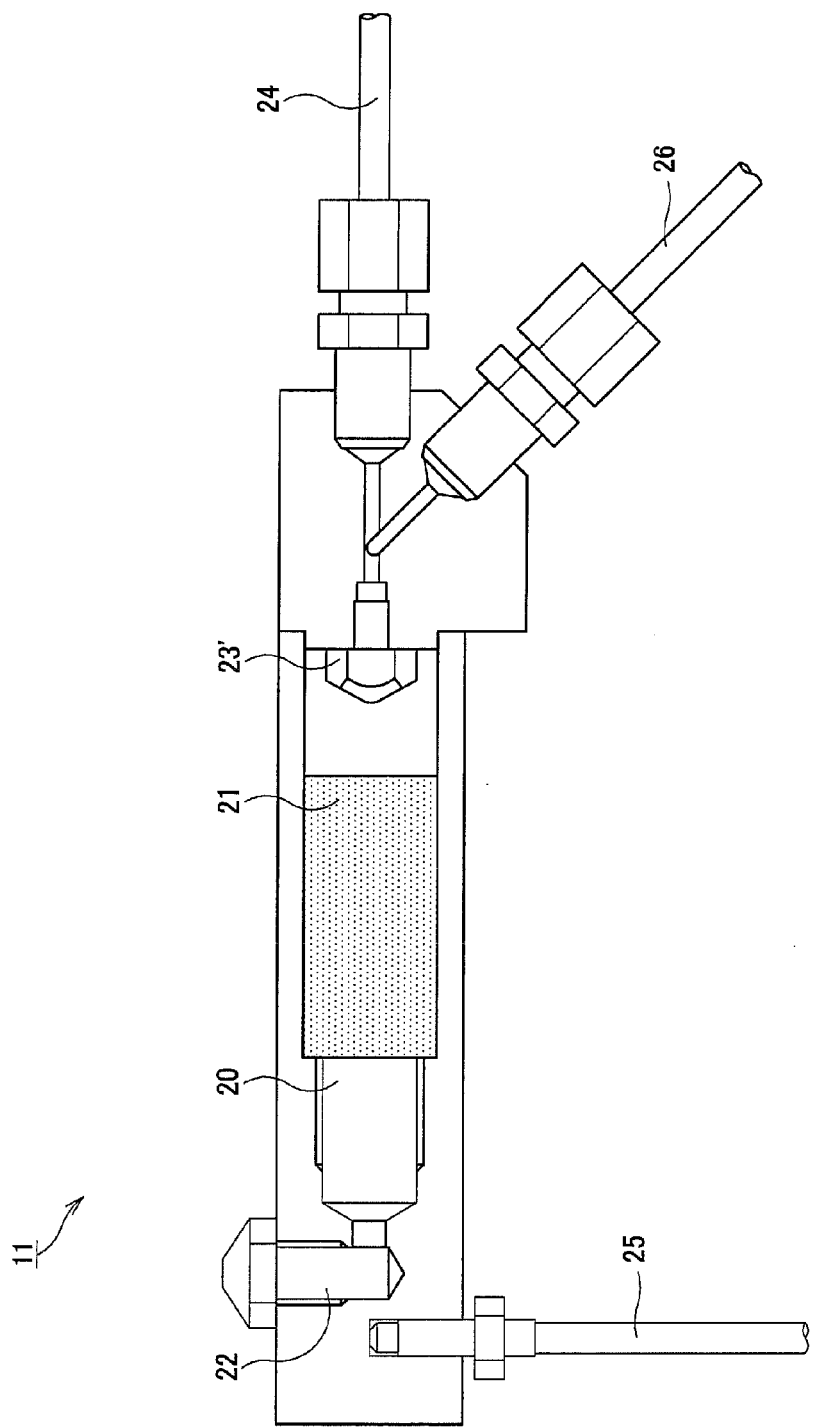
FIG. 3 is a schematic view showing a methanol gas generation device that composes an MR gas generation device according to a modification of the present invention.
Figure 4:
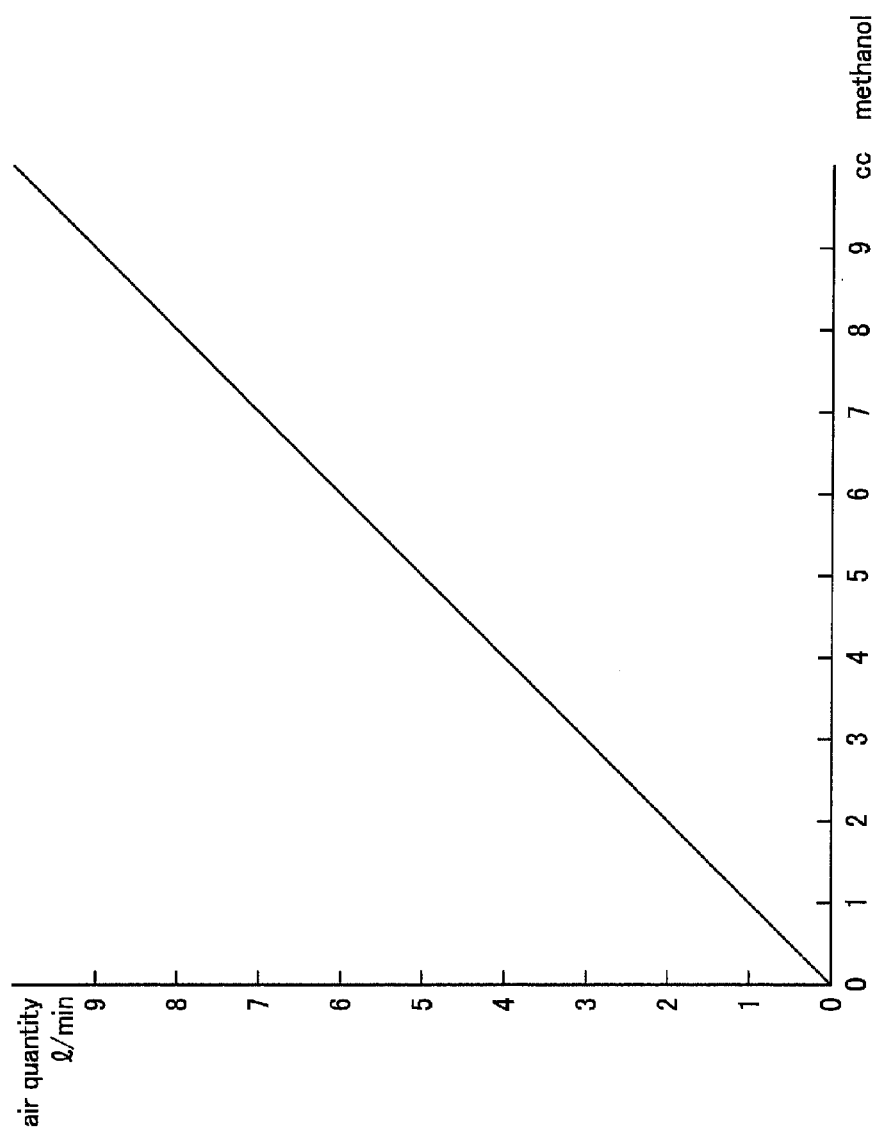
FIG. 4 is a graph showing the relationship between the quantity of methanol and that of air supplied in an MR gas generation device according to the modification.

In a modification, shown in FIG. 3, a methanol supplying communication tube 24 is connected to the methanol gas generation unit 11 to supply methanol from a methanol tank, while water is supplied in a predetermined proportion from a water tank, not shown. This water tank is connected via a water-supplying communication tube 26 to the methanol gas generation unit 11. In this case, the additional nozzle 23 may be implemented as a mixing nozzle 23' that mixes methanol supplied from the methanol tank via the methanol supplying communication tube 24 with water supplied from the water tank via the water supplying communication tube 26. The mixing nozzle 23' mixes methanol and water together, and the resulting mixture of methanol and a predetermined proportion of water is turned by e.g., a pump into a mist which is sprayed onto the thermal medium 21. By so doing, it is possible to vaporize methanol, containing water at a predetermined proportion, under a stabilized state of a constant temperature.

In sterilizing processing, it is necessary to maintain a sterilizing environment at a predetermined humidity in a well-known manner. For example, if the DNA of a virus, for example, is destroyed to provide a DNA-free environment, it is necessary to carry out processing of sterilization in a sterilized environment in which the relative humidity is maintained at ca. 75%. However, if, in carrying out the processing of sterilization by an MR gas, the MR gas exposure environment is to be adjusted to a state of predetermined humidity, such as a humidity of ca. 75%, certain environment adjustment time is needed. In addition, the predetermined humidity condition needs to be managed to be constant. It is thus extremely difficult to maintain an environment of constant humidity.

In light of the above, a predetermined amount of water is mixed into methanol from the methanol tank, at a stage of generating the methanol gas, such as to generate methanol containing water at a predetermined proportion. A methanol gas is generated from this water-containing methanol to generate an MR gas. By so doing, an effective processing for sterilization may be achieved without adjusting the humidity of the sterilizing environment beforehand. The methanol gas generation unit 11 of the above described modification includes the mixing nozzle 23' capable mixing methanol and water together to get water contained in a predetermined proportion in methanol to supply the so generated water-containing methanol as a mist. In this manner, an optimum methanol gas, maintained at a predetermined humidity, may efficiently be generated and supplied to the catalyst cartridge 13. The MR gas, generated by a catalyzed reaction from the methanol gas, is used for realization of effective processing for sterilization. There is thus no necessity to maintain and control the environment to a predetermined humidity.

The methanol gas generation unit 11, thus provided with the additional nozzle 23, is capable of spraying methanol in a mist in such a manner that methanol may be vaporized under a constant temperature range free of temperature variations. It is thus possible to generate a catalyzed turn-into-radical reaction in stability in the catalyst cartridge 13. The additional nozzle 23 may also be formed as the mixing nozzle 23' which mixes methanol with, for example, water at a predetermined proportion to enable the resulting methanol-water mixture to be supplied as a mist. It is thus possible to efficiently generate a methanol gas, maintained at a predetermined humidity, to generate the MR gas that may be used for effective processing for sterilization.

To control the temperature in the methanol gas generation unit 11 to generate and supply the methanol gas in stability, a thermocouple 25 may further be provided to manage and control the temperature. By thus providing the thermocouple 25 to manage and control the temperature, it is possible to prevent ignition of methanol to assure higher operational safety.

A metal mesh, not shown, may preferably be applied to a sidewall section of the vaporizing cover 14 that covers the vaporizing nozzle 22 that in turn provides a path for the methanol gas generated on vaporization by heating. By applying the metal mesh on the sidewall section of the vaporizing cover 14 that provides the path for the methanol gas generated, it is possible to have the methanol gas dispersed uniformly to enable the catalyzed uniform turn-into-radical reaction to take place in the catalyst cartridge 13.

The tubular section 12 of the MR gas generation device 10 of the present embodiment will now be explained. The tubular section 12 provides a path to conduct the methanol gas from the methanol gas generation unit 11 to the catalyst cartridge 13 as a site of the catalyzed turn-into-radical reaction of the methanol gas supplied from the methanol gas generation unit 11. The tubular section 12 also acts as a site where the methanol gas is mixed with air at a predetermined proportion.

Specifically, the tubular section 12 is partitioned by a punching plate 15 into an upper tubular portion 12a and a lower tubular portion 12b. The punching plate 15 operates as a gas flow streamlining element that trims the gas flow towards the upper tubular portion 12a of the methanol gas supplied from the methanol gas generation unit 11 via the vaporizing nozzle 22. The punching plate 15 also performs the role of partitioning the inside of the tubular section 12 into upper and lower parts.

The lower tubular portion 12b of the tubular section 12, delimited by the punching plate 15, represents a space filled with the methanol gas supplied from the methanol gas generation unit 11. This space is kept oxygen-free. On the other hand, the upper tubular portion 12a above the punching plate 15 is supplied with air from an air supply unit, not shown. The air is supplied at a predetermined proportion to the methanol gas so as to be mixed with the methanol gas. The methanol gas-air mixture is moved to above the tubular section 12 and flows through the catalyst cartridge 13 provided on the top of the tubular section 12. The methanol gas-air mixture is turned into radicals by the catalyzed reaction to generate an MR gas.

There is no particular limitation to the punching plate 15 used in the present embodiment. Specifically, punched holes (vent holes) formed in the surface of the punching plate, through which the methanol gas flows, may be circular—or square-shaped or of any other suitable shape. There is again no particular limitation to the size of the vent holes of the punching plate 15. Preferably, however, the hole size is not larger than 3 mm. By setting the hole size to not larger than 3 mm, it is possible to prevent the passage of the reaction heat generated by the catalyzed reaction that may take place in the catalyst cartridge 13, as later explained, thereby assuring higher operational safety.

Although the punching plate 15 is here used, it may not necessarily be the punching plate that separates the upper tubular portion 12a and the lower tubular portion 12b from each other. It is sufficient that the separating member is formed by a plate of a porous metal material that is provided with holes not larger than 3 mm, is not heat conductive and that is resistant to inflammation. Although there is no limitation to the metal material, it is preferably formed of stainless steel, for example, and has its surface polished to permit heat reflection for assuring higher operational safety.

In the upper tubular portion 12a of the tubular section 12, partitioned by the punching plate 15, the methanol gas and air are mixed together at predetermined proportions. This air is supplied via an air supply port 16, provided in the upper tubular portion 12a, from an air supply unit, not shown, connected to the upper tubular portion 12a. The air is supplied from the air supply unit via the air supply port 16 in a quantity substantially proportionate to the quantity of methanol supplied.

The supply of the air to the upper tubular portion 12a will now be explained in detail. In the MR gas generation device 10, the quantity of the air supplied to the upper tubular portion 12a may be controlled to control the temperature of the catalyzed turn-into-radical reaction brought about by the self-reaction in the catalyst cartridge 13, as later explained.

The catalyst cartridge 13 in the MR gas generation device 10, explained later in detail, is formed of a turn-into-radical reaction catalyst layer 30, which is a metal sheet shaped to a honeycomb structure to increase contact surface area with the methanol gas to enhance the reaction efficiency. In this case, it is only necessary in the catalyst cartridge 13 to apply heating to ca. 230 to 250° C. for ten and odd minutes directly after start of the operation. As from the time of end of heating, the temperature is raised up to 450 to 500° C., necessary for the turn-into-radical reaction, by stable self-reaction (catalyzed combustion reaction of the methanol gas). The catalyst cartridge 13 may be maintained at the reaction temperature and, in a manner distinct from the conventional system, it is unnecessary to perform the heating incidentally to maintain the reaction temperature for all time. Thus, in the MR gas generation device 10, no continued heating to maintain the reaction temperature is required, such that, by stabilized self-reaction, the temperature may be raised to and maintained at a temperature necessary for the reaction. Hence, the temperature necessary for the turn-into-radical reaction may readily be controlled by changing the supply quantity of air in the upper tubular portion 12a.

The MR gas generation device 10 thus operates in a manner distinct from the conventional MR gas generation device that uses a catalyst obtained on mixing metal pipes and diatomaceous earth in disordered state. That is, in the MR gas generation device 10, the catalyzed turn-into-radical reaction is caused to occur by passing the methanol gas through the catalyst cartridge 13 obtained on shaping a thin metal sheet to a honeycomb structure. By so doing, the temperature of the catalyzed reaction may readily be controlled by changing the quantity of the air supplied, in a manner free from variations that might be caused in the catalyzed reaction of the methanol gas.

Specifically, to get the temperature of the order of 450° C., needed for the catalyzed turn-into-radical reaction, by the self-reaction, air is supplied in a quantity substantially proportionate to the quantity of the methanol gas supplied, as described above. In more detail, in case the supply quantity of methanol is 3 cc, the air is supplied in a quantity corresponding to approximately 3.5 lit/min.

On the other hand, to get the temperature approximate to ca. 500° C., which is higher than 450° C., needed for the catalyzed turn-into-radical reaction, the quantity of air supplied is set so as to be larger than the air quantity proportionate to the supply quantity of the methanol gas. Specifically, the quantity of air supplied is set so as to be larger than in the case of getting the above temperature of the order of 450° C., that is, larger than the air supply quantity which, for the supply quantity of methanol of 3 cc, is approximately 3.5 lit/min.

Figure 5:
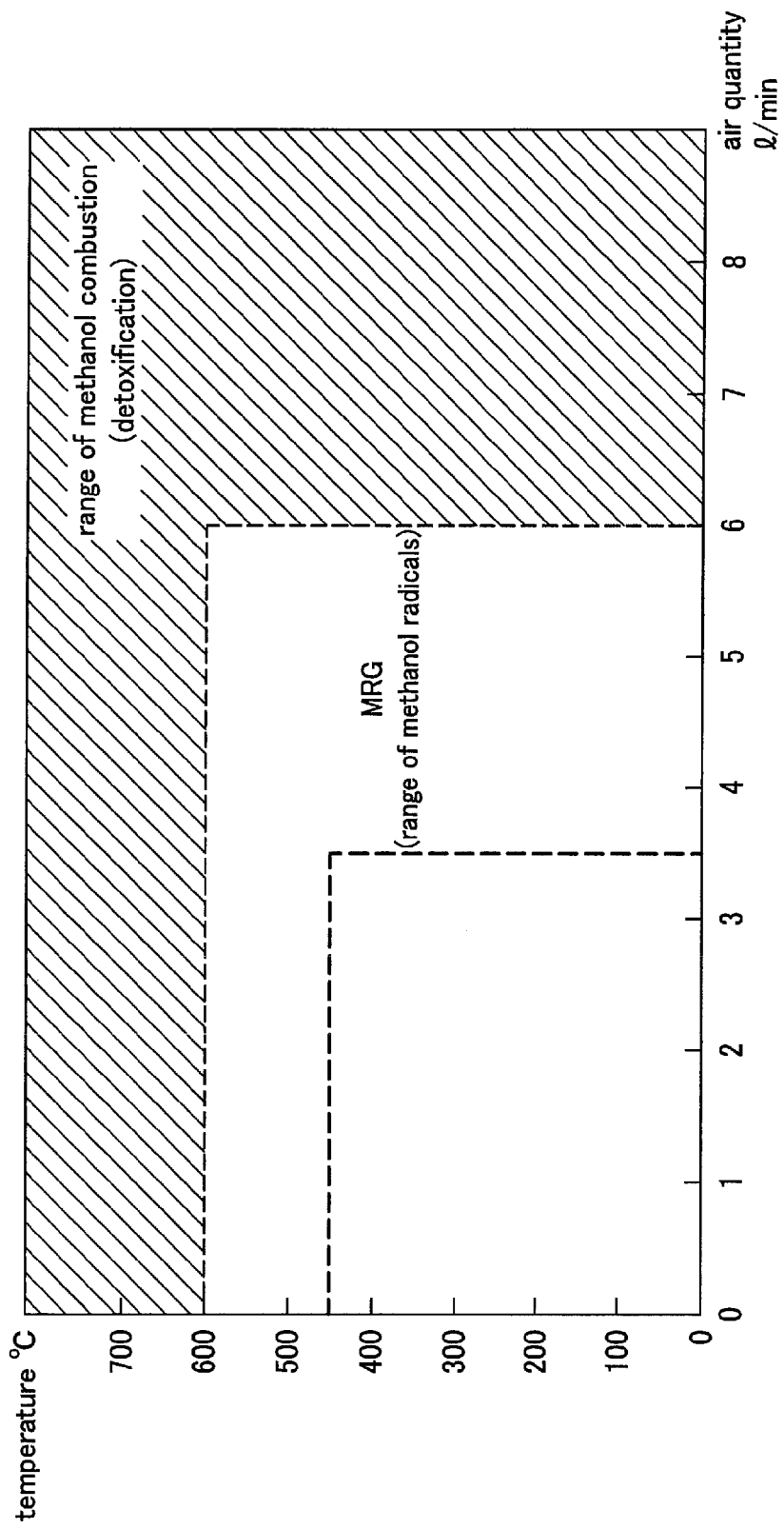
FIG. 5 is a graph for illustrating the temperature control for the catalyzed turn-into-radical reaction through changes in a quantity of air supplied in the MR gas generation device.

FIG. 5 depicts a graph for showing that, in the MR gas generation device 10, the temperature of the catalyzed turn-into-radical reaction may be controlled by changing the air supply quantity. The reaction temperature necessary for the catalyzed turn-into-radical reaction of the methanol gas is ca. 450 to 500° C. In the present MR gas generation device 10, the quantity of air supplied from the upper tubular portion 12a is varied in a range from ca. 3.5 to ca. 6.0 lit/min in relation to the quantity of supply of methanol of ca. 3.0 cc. By so doing, the temperature of the catalyzed turn-into-radical reaction may be varied in a range from ca. 450 to 500° C. The temperature of the catalyzed turn-into-radical reaction may thus be readily controlled by varying the quantity of the air from the air supply unit.

Thus, in the MR gas generation device 10 of the present embodiment, the catalyzed turn-into-radical reaction may be induced by the stabilized self-reaction without the necessity of incidental heating to maintain the catalyzed turn-into-radical reaction temperature for all time. It is thus possible to control the temperature of the catalyzed turn-into-radical reaction by simply varying the air supply quantity. On the other hand, the concentration of the MR gas generated depends on the temperature of the catalyzed turn-into-radical reaction, and hence may readily be controlled by varying the air supply quantity to control the reaction temperature in the manner described above. The MR gas concentration may thus be varied with ease from one object for sterilization to another to render it possible to perform the processing for sterilization for a wide variety of objects for sterilization.

The size of the long side of the tubular section 12, viz., the distance (L) between the methanol gas generation unit 11 and the catalyst cartridge 13, which will be explained later, is preferably set so as to satisfy the relationship: L/D=5, where (D) denotes the diameter of the tubular section 12.

Figure 6A:
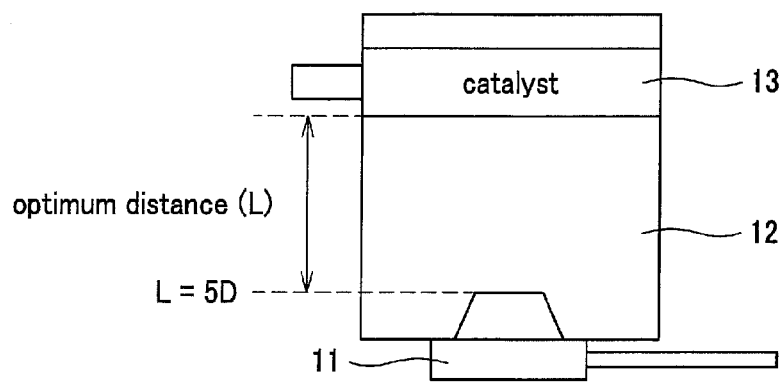
FIG. 6A is a schematic view showing an MR gas generation device in which the distance between the methanol gas generation device and the catalyst cartridge L is set so that L=5 D. And, FIG. 6B is a graph showing the relationship between the catalyst temperature and the vaporization temperature for the case of FIG. 6A.
Figure 6B:
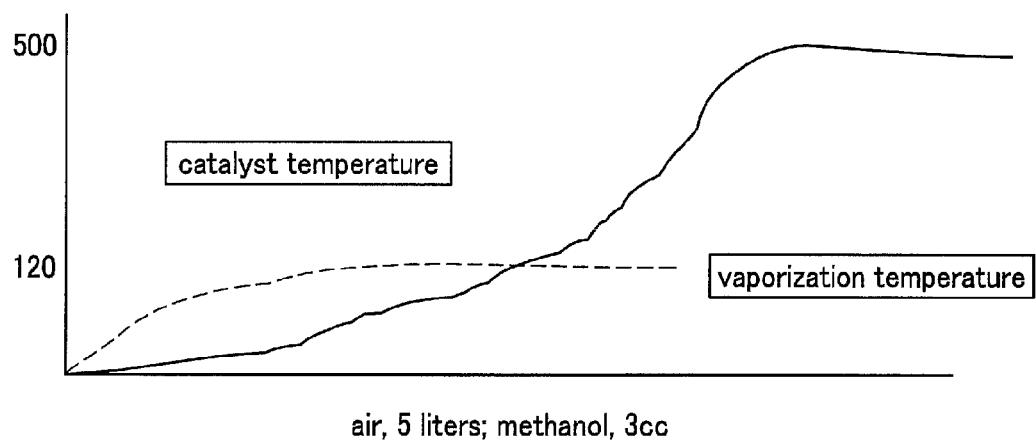

FIG. 6(A) depicts a schematic view showing a case where the distance between the methanol gas generation unit 11 and the catalyst cartridge 13 is set to satisfy the relationship L/D=5. FIG. 6(B) depicts a graph showing the results of an experiment on the relationship between the catalyst temperature and the vaporization temperature of the configuration of the MR gas generation device 10 illustrated. Referring to the graph of FIG. 6(B), in case the above distance is set to satisfy the relationship L/D=5, the catalyzed turn-into-radical reaction occurred in the catalyst cartridge 13 at a stabilized temperature and the MR gas of the high concentration of 1500 ppm could be generated in high stability. It is observed that, in the experiment shown by the graph, the quantity of air supplied is set at 5 lit/min, while that for methanol is set at 3 cc.

Figure 7A:
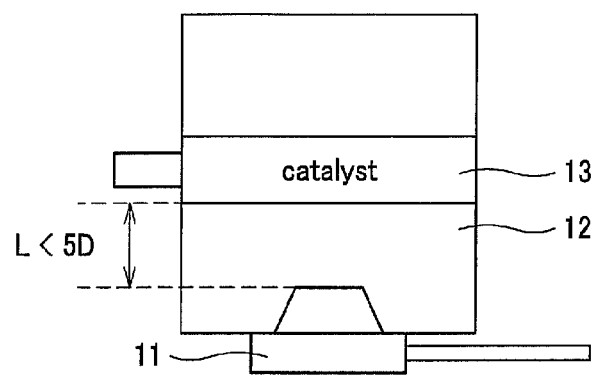
FIG. 7A is a schematic view showing an MR gas generation device in which the distance between the methanol gas generation device and the catalyst cartridge L is set so that L<5 D. And, FIG. 7B is a graph showing the relationship between the catalyst temperature and the vaporization temperature for the case of FIG. 7A.
Figure 7B:
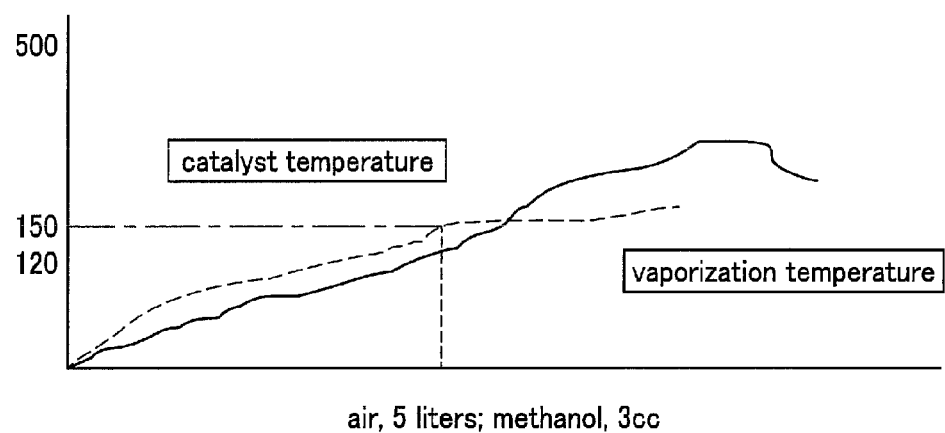

FIG. 7A depicts a schematic view showing a case where the distance between the methanol gas generation unit 11 and the catalyst cartridge 13 is set so that L/D<5. FIG. 7B depicts a graph showing the result of an experiment concerning the relationship between the catalyst temperature and the vaporization temperature for the configuration of FIG. 7A. As may be seen from the graph of FIG. 7B, in case the above distance is set so that L/D<5, the vaporization temperature of methanol was elevated to as high as 150° C. On the other hand, the reaction temperature of the catalyzed turn-into-radical reaction in the catalyst cartridge 13 was not constant but is labile. The reaction temperature necessary for turning the methanol gas into radicals may not be reached such that the MR gas may not be generated in stability.

Figure 8A:
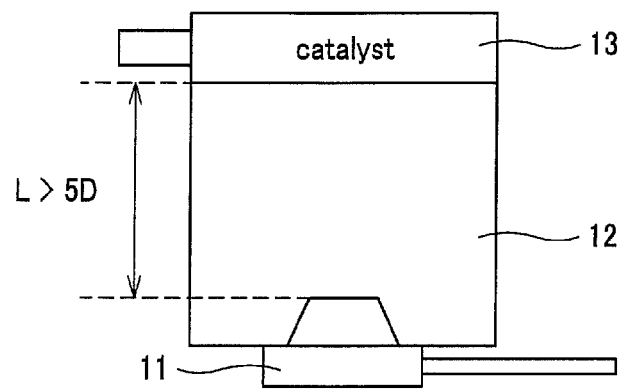
FIG. 8A is a schematic view showing an MR gas generation device in which the distance between the methanol gas generation device and the catalyst cartridge L is set so that L>5 D. And, FIG. 8B is a graph showing the relationship between the catalyst temperature and the vaporization temperature for the case of FIG. 8A.
Figure 8B:
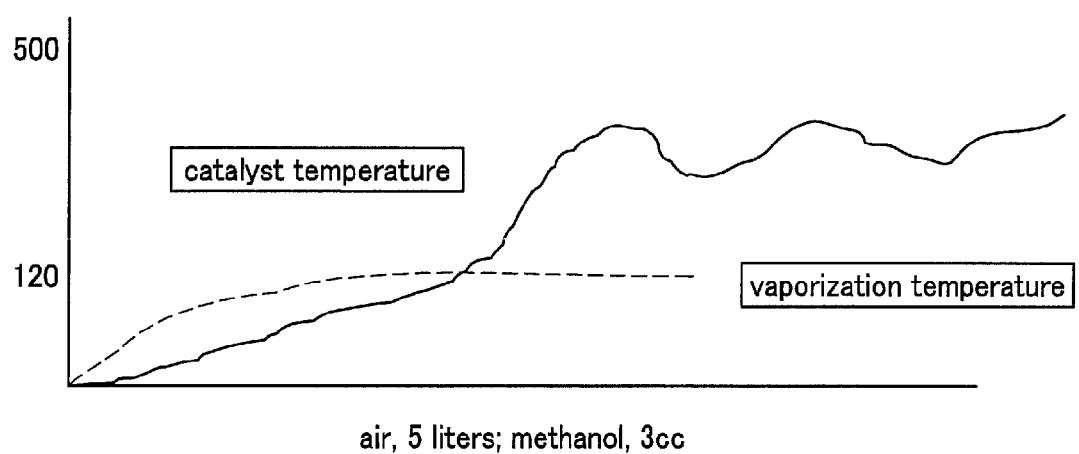

FIG. 8A depicts a schematic view showing a case where the distance between the methanol gas generation unit 11 and the catalyst cartridge 13 is set so that L/D>5. FIG. 8B depicts a graph showing the result of an experiment concerning the relationship between the catalyst temperature and the vaporization temperature for this configuration. As may be seen from the graph of FIG. 8B, in case the above distance is set so that L/D>5, the vaporization temperature was stabilized at approximately 120° C., however, the temperature of the catalyzed turn-into-radical reaction in the catalyst cartridge 13 was not constant but labile. The reaction temperature necessary for turning the methanol gas into radicals may not be reached such that the MR gas may not be generated in stability. It is observed that, in the experiment shown in FIGS. 7 and 8, the quantity of air supplied is set at 5 lit/min, while that of methanol is set at 3 cc.

As may be seen from this result of the experiment, the vaporization temperature for methanol may be stabilized by setting the distance between the methanol gas generation unit 11 and the catalyst cartridge 13 so that L/D=5 is met. On the other hand, the temperature of the catalyzed turn-into-radical reaction in the catalyst cartridge 13 may be made constant to render it possible to generate the MR gas in safety and high stability.

The catalyst cartridge 13 as a component of the MR gas generation device 10 according to the present embodiment will now be described. The catalyst cartridge 13 operates so that the methanol gas, generated by the methanol gas generation unit 11 and mixed with air at a predetermined proportion in the tubular section 12, is allowed to undergo a decomposition reaction by the catalyzing action based on the self-reaction. By this decomposition reaction, the methanol gas is turned into radicals to generate an MR gas.

Figure 9:
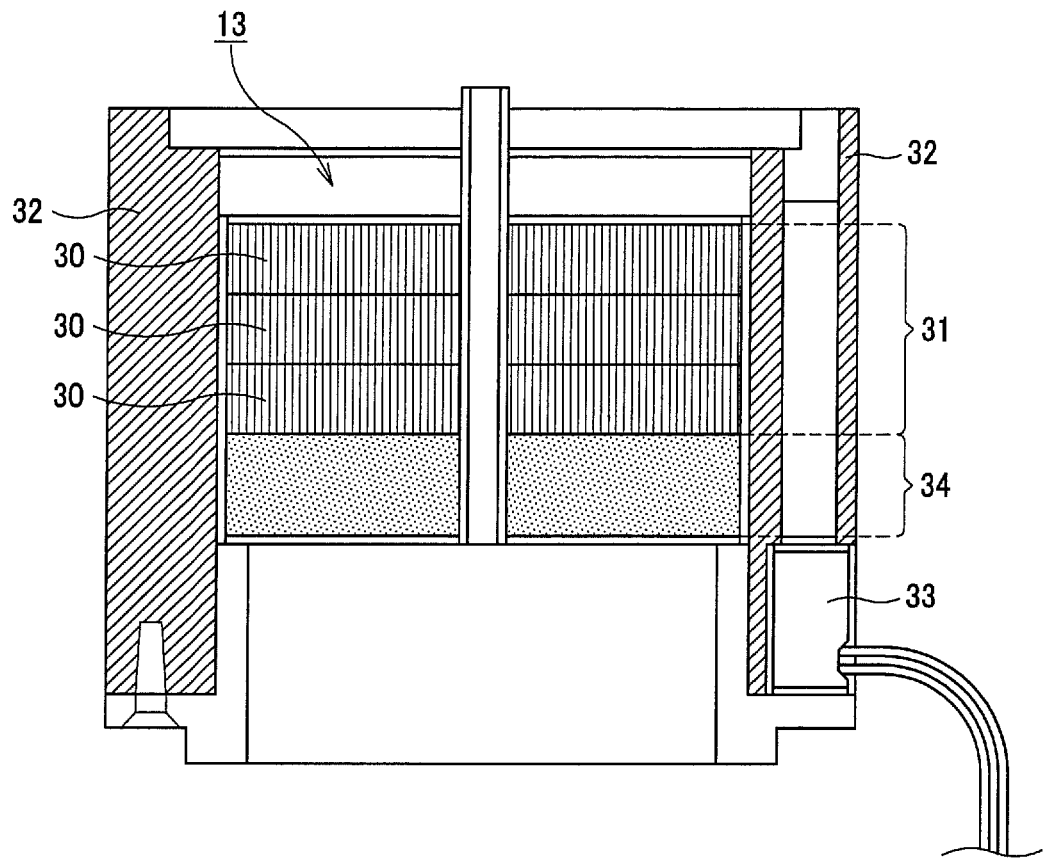
FIG. 9 is a schematic view showing a catalyst cartridge composing the MR gas generation device.

FIG. 9 depicts a schematic view showing the structure of the catalyst cartridge 13 and its outer peripheral section. Referring to FIG. 9, the catalyst cartridge 13 includes a catalyst layer assembly 31 formed by a plurality of turn-into-radical catalyst layers 30 each of which is of a honeycomb structure. The catalyst cartridge also includes a catalyst heating block 32, arranged for surrounding the catalyst layer assembly 31, and an electrical heater 33 configured for temporarily heating the catalyst cartridge 13. The methanol gas, moved into the catalyst cartridge 13 by natural convection through the tubular section 12, is subjected to a vigorous decomposition reaction by the catalyzed action by self-reaction in the catalyst cartridge 13 so as to be thereby turned into an MR gas. The MR gas, generated in the catalyst cartridge 13, exits the catalyst cartridge 13 to move into a space in which to process an object being sterilized.

The catalyst cartridge 13, constructed as described above, includes a turn-into-radical reaction catalyst layer 30 formed from a thin metal sheet to a corrugated structure. The thin metal sheet is referred to below by a reference numeral 35a. When the methanol gas, generated by heating to 129 to 130° C. in the methanol gas generation unit 11, is moved into the catalyst cartridge 13, it is heated to 230 to 250° C. by the electric heater 33 for approximately 15 to 20 minutes as from the start of the operation. Thereafter, as the catalyzed combustion of the methanol gas (self-reaction) is initiated, the operation of the electric heater 33 is discontinued. The reaction temperature is allowed to rise by the self-reaction up to approximately 450 to 500° C. which is necessary for the turn-into-radical reaction. This temperature is then maintained. A more specific explanation will now be made beginning from the explanation of the structure of a turn-into-radical reaction catalyst layer 30 that composes a honeycomb structure.

Figure 10:
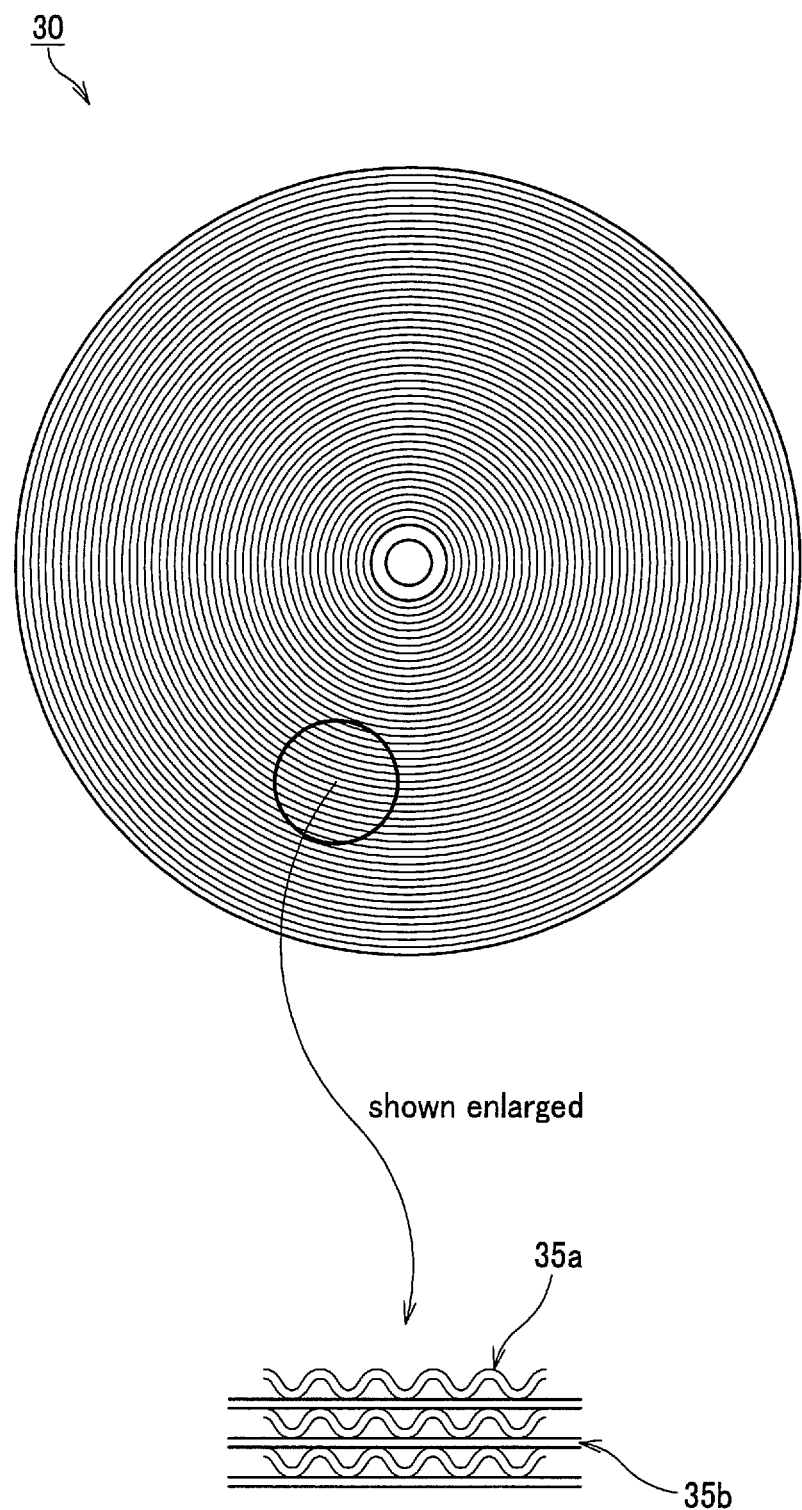
FIG. 10 upper part is a schematic view, as seen from above, showing a turn-into-radical reaction catalyst layer of a catalyst cartridge composing the MR gas generation device. And, also (lower part) is an enlarged schematic side view showing a portion of the catalyst of FIG. 10 (upper part).

The turn-into-radical reaction catalyst layer 30 that forms the catalyst cartridge 13 is comprised of a honeycomb structure which is the thin metal sheet 35a worked to a corrugated shape. An upper part of FIG. 10 depicts a schematic view of the structure of the turn-into-radical reaction catalyst layer 30 when seen from above. The turn-into-radical reaction catalyst layer 30 thus is cylindrically shaped. A lower part of FIG. 10 depicts an enlarged schematic side view of a portion of the honeycomb structure. More specifically, the turn-into-radical reaction catalyst layer 30 is composed of a plurality of the corrugated thin metal sheets 35a worked to a corrugated shape sandwiched between planar thin metal sheets. Each planar thin metal sheet is referred to below by a reference numeral 35b. The corrugated metal sheets and the planar thin metal sheets are alternately arranged to form the honeycomb structure which is then bent to a cylindrical shape.

It is observed that the shape of the catalyst cartridge 13 is not limited to the cylindrical shape described above. For example, the corrugated thin metal sheets 35a and the planar thin metal sheet 35b may be alternately stacked together in similar manner and worked to a variety of shapes, including a square prismatic or polyhedral prismatic shape. Moreover, the shape of the honeycomb structure that composes the turn-into-radical reaction catalyst layer 30 is not limited to the corrugated shape, but may also be a chevron shape. The corrugated shape is also not limited to that shown as an example in the partial enlarged side view of FIG. 10. For example, the corrugated thin metal sheets 35a, arranged in alternation with the planar thin metal sheets 35b, may be arranged offset relative to the neighboring corrugated thin metal sheets 35a so as to provide a phase shift relative to the corrugations of the neighboring thin metal sheets 35a. By arranging the neighboring corrugated thin metal sheets 35a so as to provide such phase shift, the contact surface of the methanol gas may further be increased to further improve the reaction efficiency.

The reaction catalyst layer in a conventional MR gas generation device has a diametrical size as large as 150 to 180 mm in case it is assumed that the catalyst has a circular upper surface. This accounts for the larger size of the MR gas generation device and renders it difficult to reduce the overall device size. Moreover, in the conventional reaction catalyst layer, having a diameter as large as 150 mm or more, it is necessary to generate heat of the order of 450 to 500° C., necessary for the turn-into-radical reaction, as from the time of the start of the operation, with the use of an electrical heater. After heat generation, the temperature may not be maintained for an extended time period because of the large size of the reaction catalyst layer, such that heating needs to be performed using the electrical heater by way of follow-up heating. In case the catalyzed reaction is carried out in this manner as the follow-up heating is used, it is naturally difficult to maintain a constant turn-into-radical reaction temperature, and hence the MR gas having a stable concentration may not be generated. In addition, the electrical heater is to be provided to repeat the heating from time to time to maintain the temperature necessary for the turn-into-radical reaction in the catalyst. This renders it difficult to use a simplified cartridge configuration MR gas generation device in which the catalyst by itself may be exchanged at a desired time, thus further enlarging the size of the device.

Further, the reaction catalyst layer used in the conventional MR gas generation device is formed by mixing e.g. diatomaceous earth and metal pipes in disorderly state, such that it is not possible to provide a sufficient surface for reaction. Moreover, a methanol gas passage may not be provided steadily such that only non-uniform turn-into-radical reaction suffering from variations may be induced for the methanol gas. This in turn proves to be a factor responsible for temperature variations of the turn-into-radical reaction.

In the MR gas generation device according the present embodiment, the catalyst cartridge 13 is formed by the turn-into-radical reaction catalyst layer 30 obtained on forming thin metal sheets to a honeycomb structure. By so doing, the contact surface between the methanol gas and the turn-into-radical reaction catalyst layer 30 may be increased, while the methanol gas is allowed to pass through a constant route.

By forming the turn-into-radical reaction catalyst layer 30 to a honeycomb structure to increase its contact surface with the methanol gas, it is possible to elevate the reaction efficiency of the catalyzed reaction as well as to suppress the size of the catalyst cartridge 13 necessary for the turn-into-radical reaction to a minimum. More concretely, the diametrical size of the turn-into-radical reaction catalyst layer 30 in the catalyst cartridge 13 may be of the order of 50 to 70 mm. With this extremely small size, the turn-into-radical reaction may be induced with a high reaction efficiency. By suppressing the size of the catalyst cartridge 13 to this extremely small value, the catalyst cartridge may be of a readily exchangeable configuration. In addition, by having the methanol gas pass through the constant route, it is possible to suppress variations of the turn-into-radical reaction to provide for a steady-state reaction as well as to reduce variations in the reaction temperature.

Furthermore, in the reaction catalyst layer for the conventional MR gas generation device, it is necessary to maintain the temperature necessary for the turn-into-radical reaction by carrying out the reaction as the catalyst is heated by the electrical heater. On the other hand, the turn-into-radical reaction catalyst layer 30 of the present embodiment is worked to a honeycomb structure to enhance its contact surface, so that it is possible to efficiently carry out the turn-into-radical reaction in stability. The predetermined temperature necessary for the turn-into-radical reaction may be maintained to generate the MR gas of stable concentration without the necessity of performing incidental heating with the use of the electrical heater 33.

Specifically, the temperature may be elevated to ca. 450 to 500° C. necessary for the turn-into-radical reaction by solely the heating to ca. 230 to 250° C. by the electrical heater 33 for approximately 15 to 20 minutes directly after start of the operation, followed by the self-reaction in the turn-into-radical reaction catalyst layer 30. The constant temperature may then be maintained to allow an MR gas of a stabilized concentration to be generated without the necessity of heating incidentally by the electrical heater. Since such heating by the electrical heater incidentally is unneeded, there is no necessity of providing the electrical heater 33 within the catalyst. The catalyst may be of a cartridge configuration that may be exchanged with ease to render it possible to reduce the size of the overall device.

The temperature keeping state in the self-reaction of the catalyst cartridge 13 having the honeycomb structure will now be described in further detail.

In the conventional MR gas generation device, the reaction catalyst layer is of a larger size and is formed by mixing e.g. diatomaceous earth and metal pipes in disorderly state. It has thus been difficult to keep a constant temperature required for the turn-into-radical reaction. Moreover, follow-up heating has to be carried out from time to time, resulting in temperature variations not less than ±20° C. in the catalyzed reaction temperature. These temperature variations not less than ±20° C. significantly affect the concentration of the MR gas generated to render it not facile to generate an MR gas at a stabilized concentration.

Figure 11:
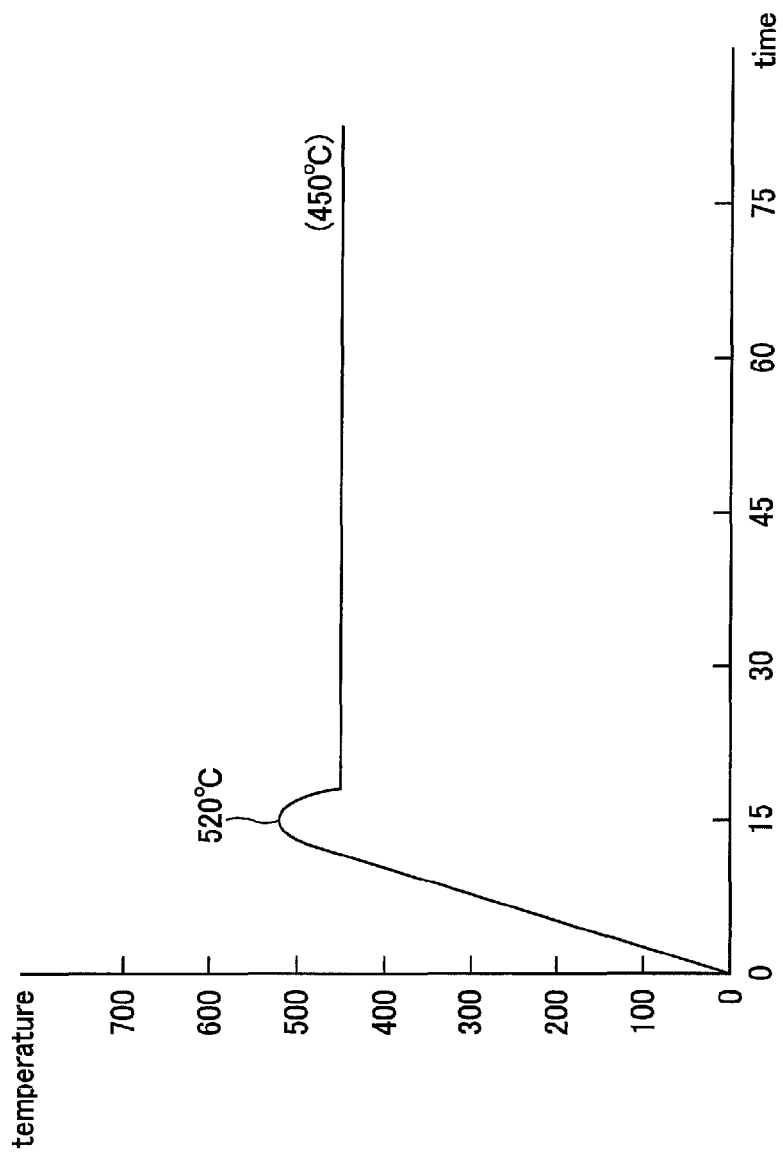
FIG. 11 is a graph showing changes in temperature of the catalyzed reaction in the catalyst cartridge composing the MR gas generation device.

In the MR gas generation device 10 of the present embodiment, provided with the catalyst cartridge 13 having the honeycomb structure, shown in FIG. 11, in which the reaction efficiency is improved, the turn-into-radical reaction may be carried out in a manner free of temperature variations. Specifically, the temperature of ca. 450 to 500° C., necessary for the turn-into-radical reaction, may be maintained in stability simply by heating by the electrical heater 33 provided in the device 10 for about 15 to 20 minutes to ca. 230 to 250° C., followed by the self-reaction. It is thus possible to realize a turn-into-radical reaction free of temperature variations.

Also, the catalyst cartridge 13 is formed by the turn-into-radical reaction catalyst layer 30 of the honeycomb structure which is obtained by arranging the corrugated thin metal sheets 35a and the planar thin metal sheets 35b in alternation with one another, as schematically shown in FIG. 10 lower part. In this manner, the surface for the catalyzed reaction as well as the pass route for the methanol gas may be defined uniquely, thus contributing to realization of the turn-into-radical reaction free of reaction variations, such as temperature variations. It is observed that, in the experiment shown in the graph of FIG. 11, the supply of methanol and that of air were set to 3 cc and 3.5 lit/min, by way of sterilization setting conditions.

It is observed that temperature variations not less than ±20° C. for the catalyzed reaction temperature are ascribable to temperature variations in the methanol gas generation device 11 as well. In the conventional MR gas generation device, temperature variations not less than ±2° C. were produced in its methanol gas generation device. In the methanol gas generation unit 11 of the MR gas generation device 10 of the resent embodiment, not only the thermal medium 21 but also the components of the methanol gas generation unit 11 are formed by a material which is highly effective to maintain the constant temperature, as described above. It is thus possible to suppress temperature variations in the methanol gas generation unit 11. Since the methanol gas generation unit 11 is formed from the material which is highly effective to maintain the constant temperature, it becomes possible to evenly apply heat to methanol to vaporize it under temperature control to 120 to 130° C. substantially free of temperature variations which are just of the order of ±0.5° C. The MR gas may be generated at a stabilized concentration as catalyzed reaction temperature variations in the catalyst cartridge 13 are suppressed. In addition, in the methanol gas generation unit 11, methanol supplied from the methanol tank is sprayed in a mist for heating and vaporization, as described above. In this manner, the methanol gas may be generated in a stabilized state at a constant temperature, so that the MR gas may be generated at a stabilized concentration as variations in the temperature of the methanol gas generation unit 11 are further suppressed to generate the MR gas at the stabilized concentration.

The honeycomb structure that composes the turn-into-radical reaction catalyst layer 30 may be formed from a variety of transition metals, such as copper (Cu), platinum (Pt) or nickel (Ni). In the present embodiment, copper, for example, is used and thin copper sheets are worked to a corrugated shape, for example, to provide a honeycomb structure to increase the surface for the reaction to provide for a stabilized self-reaction. In more detail, thin copper sheets are worked to the corrugated shape to increase the surface and stacked in alternation with planar copper sheets to create interstices necessary for the reaction.

In this manner, the thin copper sheets 35a are worked to the corrugated shape, for example, and stacked in alternation with the planar copper sheets 35b to increase the contact surface. By so doing, the methanol gas may be efficiently reacted to generate the MR gas of a constant concentration, with the diametrical size of the turn-into-radical reaction catalyst layer 30 of the order of 50 to 70 mm, without the necessity of incidental heating to a temperature necessary for the turn-into-radical reaction. Moreover, since the interstices necessary for the reaction are created, and the methanol gas may travel in a steady state through the so created interstices, it is possible to realize a stable catalyzed turn-into-radical reaction to suppress temperature variations. It is observed that the corrugated thin metal sheet 35a and the planar thin metal sheet 35b, stacked in alternation with one another to provide the honeycomb structure, may be of the same metal, or different metals.

Furthermore, the reaction efficiency may be equivalent to or higher than in the conventional system without the necessity of forming a reaction catalyst layer by kneading pulverized diatomaceous earth with a porous member fabrication assistant agent to form a catalyst carrier, and by coating the so formed catalyst carrier with metal, such as platinum, as conventionally. The cost of device fabrication may also be reduced. In addition, the turn-into-radical reaction catalyst layer with high reaction efficiency may readily be prepared as the labor of kneading pulverized diatomaceous earth with other agents may be dispensed with.

In the MR gas generation device 10 according to the present embodiment, a plurality of the turn-into-radical reaction catalyst layers 30, each formed to the honeycomb structure, as described above, may be stacked together to form the multi-layered catalyst layer assembly 31. In case the thin metal sheets 35a of the turn-into-radical reaction catalyst layer 30 that make up the catalyst layer assembly 31 are worked to a corrugated shape to provide the honeycomb structure, it is more preferred to phase-shift the corrugations of the thin metal sheets 35a in forming the turn-into-radical reaction catalyst layers 30 stacked together.

Figure 12B:
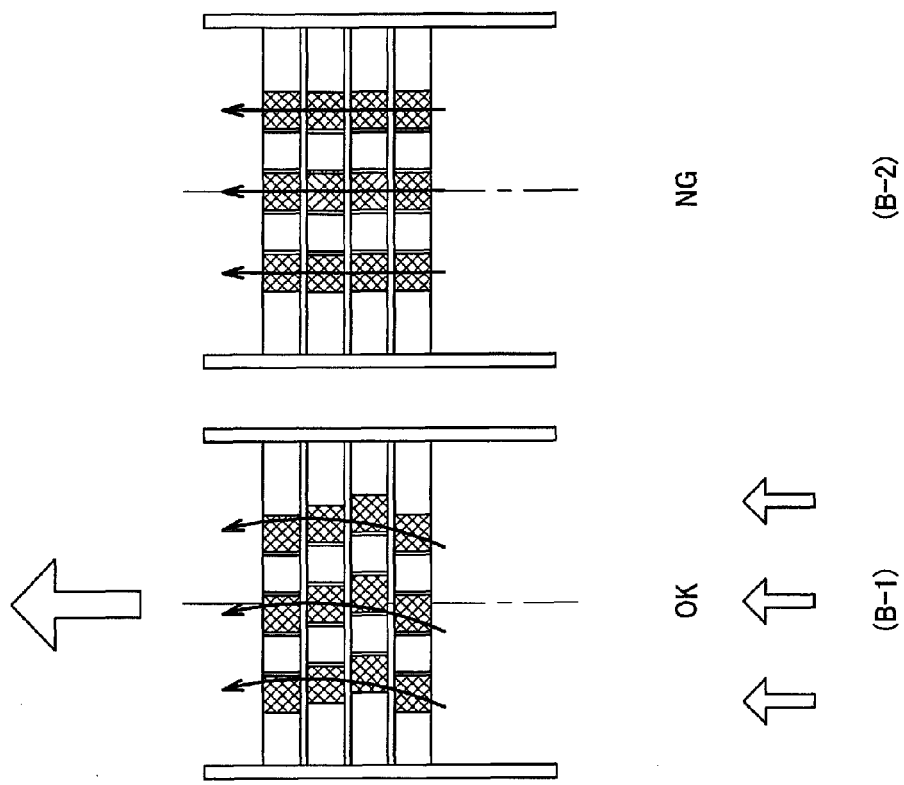
FIG. 12A is a schematic view, seen from above, and showing the turn-into-radical reaction catalyst layer of the catalyst cartridge composing the MR gas generation device, in case the catalyst is formed as an assembly composed of a plurality of turn-into-radical reaction catalyst layers stacked together, in which the turn-into-radical reaction catalyst layers are stacked with phase shift. And, FIGS. 12B (B-1), (B-2) are schematic side views of the catalyst assembly for illustrating the methanol gas flow in case the turn-into-radical reaction catalyst layers are stacked with phase shift (B-1) and in case the turn-into-radical reaction catalyst layers are stacked without phase shift (B-2).
Figure 12A:
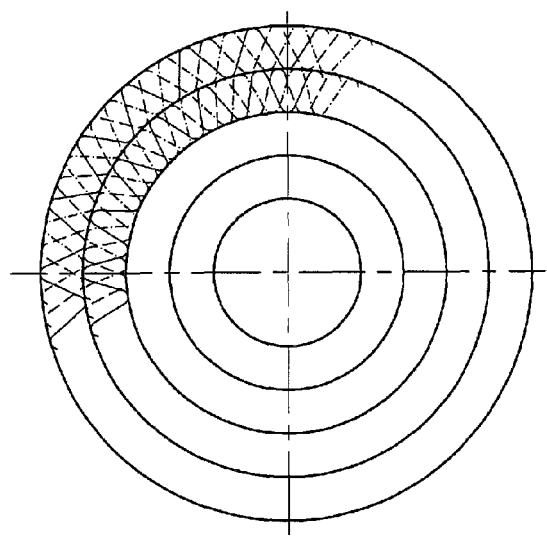

FIG. 12A depicts a schematic view, seen from above, of the catalyst cartridge 13 applied to the MR gas generation device 10, specifically illustrating the phase states of the respective turn-into-radical reaction catalyst layers 30. FIG. 12B shows the flow of a vaporized gas in case where the corrugations of the turn-into-radical reaction catalyst layers 30 that compose the catalyst layer assembly 31 are formed with phase shift (B-1) and in case the corrugations are formed without phase shift (B-2). The catalyst layer assembly 31 may be formed so that the corrugations of the thin metal sheets 35a of the turn-into-radical reaction catalyst layers 30 are phase-shifted, as shown in FIG. 12A. It is observed that the phases of the corrugations of the thin metal sheets 35a composing the honeycomb structures of the respective layers are indicated by different lines, viz., solid lines, dotted lines and chain-dotted lines.

By composing the catalyst layer assembly 31 with phase shifts of the corrugations of the thin metal sheets 35a of the respective layers, the methanol gas-turn-into-radical reaction catalyst layer contact surface may further be increased to further improve the reaction efficiency of the catalyzed turn-into-radical reaction, as shown in FIG. 12B (B-1).

In the present embodiment, the catalyst cartridge 13, whose catalyst layer assembly 31 is formed by stacking three or four turn-into-radical reaction catalyst layers 30, has specifically been described with reference to FIGS. 1 and 12. However, there is no particular limitation to the number of the turn-into-radical reaction catalyst layers 30 stacked together. In case the thin metal sheets 35a are worked to e.g., a chevron shape to form the honeycomb structure, it is preferred to stack a plurality of the chevron-shaped thin metal sheets 35a with phase shift of the chevron shapes.

In the MR gas generation device 10 of the present embodiment, porous materials having high heat insulating effects, such as diatomaceous earth, silica or coarse sand, is laid on the bottom surface of the catalyst layer assembly 31 of the honeycomb structure, as shown in FIG. 1. By so doing, a radiant heat inhibiting layer 34 is formed.

In the catalyst layer assembly 31, the catalyzed turn-into-radical reaction is occurring at a temperature close to ca. 450 to 500° C. by the self-reaction, as described above. By this reaction, radiant heat of a higher temperature is evolved. Since the radiant heat inhibiting layer 34 is formed below the catalyst layer assembly 31, the high-temperature radiant heat is prevented from contacting with methanol supplied to the catalyst layer assembly 31, thus assuring operational safety. Moreover, the temperature at the catalyst layer assembly 31 may be maintained constant to permit the catalyzed reaction to occur in a stable state to high efficiency.

By forming the radiant heat inhibiting layer 34 from a material exhibiting a heat insulating effect, dissipation of heat evolved by the self-reaction of the catalyst cartridge 13 may be suppressed to allow the temperature to be maintained constant. It is also possible to reduce adverse effects the radiant heat might have on the methanol gas generation unit 11.

In preparing the catalyst cartridge 13 in the MR gas generation device 10 in the present embodiment, the corrugated thin metal sheets 35a of e.g., copper are stacked in alternation with the planar thin metal sheet 35b to form a honeycomb structure of the turn-into-radical reaction catalyst layer 30, as described above. Preferably, a plurality of the turn-into-radical reaction catalyst layers 30 of the honeycomb structure is stacked together to form the catalyst layer assembly 31. By so doing, the contact surface of the catalyst layer assembly with the methanol gas may be increased to induce an efficient turn-into-radical reaction.

Also, since the contact surface is increased to enhance the reaction efficiency, it is possible to realize the reaction efficiency equivalent to or higher than that possible with the conventional system to render it possible to reduce the size of the catalyst cartridge 31. Moreover, since the reaction efficiency has been improved, the temperature necessary for the catalyzed turn-into-radical reaction may be maintained by stabilized self-reaction without the necessity of heating from time to time to keep the catalyzed reaction temperature for the turn-into-radical reaction. There is thus no necessity to provide the electrical heater in the inside of the catalyst for incidental heating. The catalyst may thus be further reduced in size to make it possible to implement a cartridge configuration catalyst that may be exchanged extremely readily.

In addition, in the catalyst cartridge 13, the catalyzed turn-into-radical reaction is enabled by the stable self-reaction. Thus, by controlling the amount of air supplied from an air supply unit connected to the tubular section 12, in a desired manner, the temperature of the catalyzed turn-into-radical reaction by the self-reaction may readily be controlled to render it possible to change the concentration of the generated MR gas with ease. It is thus possible to readily generate the MR gas at a concentration optimum for an object being sterilized by simply changing the amount of air, supplied so as to be mixed with the methanol gas, to render it possible to perform the processing for sterilization efficient for variable objects. Moreover, since the MR gas may be generated to an optimum concentration, it is possible to suppress the amount of methanol supplied to a necessary minimum value. Hence, the device for processing for sterilization may be used in high safety, while the processing for sterilization is more amenable to environment.

A device for processing for sterilization that uses the MR gas generation device 10 according to the above described embodiment will now be described in detail.

Figure 13:
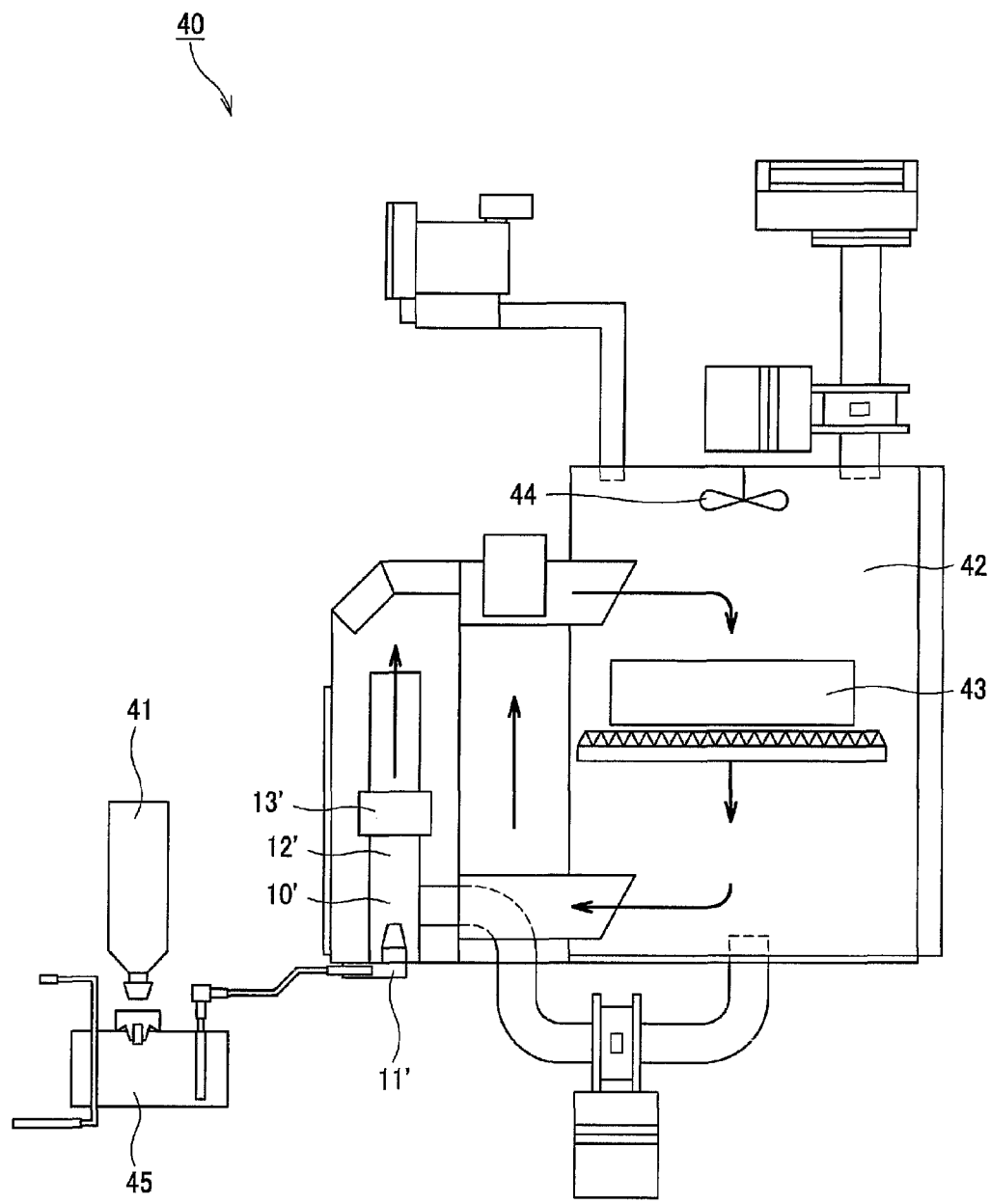
FIG. 13 is a schematic side view showing a device for processing for sterilization constructed using the MR gas generation device.

FIG. 13 depicts a schematic view showing an example of a device for processing for sterilization 40 that uses the MR gas generation device 10 according to the present embodiment. Referring to FIG. 13, the device for processing for sterilization 40 includes a methanol tank 41, an MR gas generation device 10' and a sterilization tank 42 that provides a site in which to hold an object being sterilized as well as to carry out the processing for sterilization by the MR gas generated by the MR gas generation device 10'.

The MR gas generation device 10', provided in the device for processing for sterilization 40, includes a methanol gas generation unit 11', a tubular section 12' and a catalyst cartridge 13'. Methanol is supplied from the methanol tank 41 to the MR gas generation device 10' where methanol is vaporized to yield the methanol gas. The tubular section 12' is provided on top of the methanol gas generation unit 11' to permit the methanol gas generated by the methanol gas generation unit 11' to be mixed with air as well as to cause the methanol gas generated to flow upwards by natural convection. The catalyst cartridge 13' is detachably mounted in contiguity to the tubular section 12' on top of a flow path of the methanol gas to turn the methanol gas into radicals by a catalyzed reaction. The catalyst cartridge 13' of the MR gas generation device 10', provided in the device for processing for sterilization 40, has a honeycomb structure comprised of a plurality of corrugated thin metal sheets and a plurality of planar thin metal sheets stacked in alternation with one another.

In the MR gas generation device 10' formed by the catalyst cartridge 13' of the honeycomb structure, the methanol gas may be turned efficiently into radicals to permit the MR gas of a constant concentration to be generated in stability.

The MR gas, generated by the MR gas generation device 10', is circulated through the inside of the sterilization tank 42, as indicated by arrow in FIG. 13, to sterilize an object being sterilized 43. A circulation fan 44 may be provided at an upper part of the sterilization tank 42 for efficiently circulating the MR gas within the sterilization tank 42. By circulation of the MR gas efficiently within the sterilization tank 42, it is possible to elevate the concentration of the MR gas to further improve the effect of sterilization on the object being sterilized 43.

The device for processing for sterilization 40 of the present embodiment also includes a vent unit, not shown. This vent unit is formed as a honeycomb structure obtained on stacking a plurality of corrugated thin metal sheets and a plurality of planar thin metal sheets in alternation with one another, as is the catalyst cartridge 13' of the MR gas generation device 10'. Any residual methanol gas in the device is allowed to pass through the vent unit and decomposed into a carbonic gas and water which are exhausted. This may improve operational safety in the processing for sterilization.

Although there is no particular limitation to the methanol tank 41, it is possible to use a disposable tank. For example, a methanol tank with a capacity of the order of 2 liters is used and methanol contained therein is stored in its entirety in a secondary tank 45. Methanol is sprayed from the secondary tank into the methanol gas generation unit 11'. By using up methanol in this manner, the processing for sterilization may be may be carried out with enhanced safety without allowing methanol to be left in the device. There is no necessity of providing a means for maintaining the liquid level in the secondary tank 45 and hence the device for processing for sterilization may be manufactured at a reduced cost.

Moreover, with the use of the MR gas generation device 10 according to the above described embodiment, it is possible to provide a device for processing for sterilization in which the object being sterilized 43 is not placed in a stationary position within the device for processing for sterilization 40. This device configuration is not of that of the device for processing for sterilization 40 shown in FIG. 13. Viz., the device for processing for sterilization, making use of the device for processing for sterilization 40 of the present embodiment that may now be reduced in size, may be placed in a stationary position in a confined space. The MR gas generated by the catalyzed turn-into-radical reaction device may be allowed to fill the confined space to sterilize it. By so doing, it becomes possible to sterilize the space which it has been not possible to sterilize with the conventional MR gas generation device, such as a room in a hospital or a space in a car or a vehicle.

The MR gas generation device 10 of the present embodiment includes the catalyst cartridge 13 formed by the turn-into-radical reaction catalyst layers 30 obtained by forming thin metal sheets to a honeycomb structure. This may increase the contact surface between the methanol gas and the catalyst. The catalyzed turn-into-radical reaction may thus be improved in reaction efficiency to produce a catalyzed stable self-reaction to allow an MR gas to be generated at a constant concentration.

Since the reaction efficiency of the catalyzed reaction may be improved by the turn-into-radical reaction catalyst layer 30 having the honeycomb structure, the reaction catalyst layer may be reduced in size. The reaction catalyst layer may be formed as a cartridge that may be exchanged extremely readily. Moreover, the device for processing for sterilization itself may be reduced in size, and hence objects of widely variable types may thereby be sterilized.

For example, with the use of the MR gas generation device of the present embodiment, an ambulance car transporting a patient of an infectious disease may be an object to be sterilized. A conventional device for processing for sterilization is itself bulky and difficult to transport. Moreover, the processing for sterilization is time-consuming such that a limited number of ambulance cars may not be sterilized quickly. The device for processing for sterilization that makes use of the MR gas generation device of the present embodiment is easy to transport and may be used with ease to perform the processing for sterilization. The reason is that, with the present MR gas generation device of the present embodiment, the reaction efficiency is improved and the reaction catalyst layer is reduced in size.

In addition, in the MR gas generation device 10 of the present embodiment, the turn-into-radical reaction temperature by the catalyzed self-reaction may readily be controlled by varying the quantity of air in the upper tubular portion 12a. Hence, the concentration of the MR gas generated may be controlled with ease. For example, suppose that viruses are to be exposed to the MR gas with a view to destructing their DNA. In such case, the quantity of air supplied may be increased to elevate the turn-into-radical reaction temperature to generate the MR gas to a higher concentration. Viz., the quantity of air supplied may be changed from one object for sterilization to another to cause variations in the concentration of the MR gas generated.

It is to be noted that the present invention is not limited to the above described embodiment such that any changes in configuration comprised within its scope may be comprised within the present invention.

Industrial Utilizability

According to the present invention, a turn-into-radical reaction catalyst layer, obtained on forming thin metal sheets to a honeycomb structure, is used, so that the surface in the catalyst section is increased to improve the reaction efficiency. Hence, the self-reaction may be induced as the temperature of the catalyzed reaction is kept at a constant temperature. The MR gas at a stabilized temperature may thus be generated. In addition, the catalyst section may be reduced in size due to improved reaction efficiency at the catalyst section. The device for processing for sterilization itself may be reduced in size to enhance its field of application.

The invention claimed is:

1. A device for generating a sterilizing gas comprising:
   a methanol gas generation section including a nozzle that sprays methanol supplied from a methanol tank in the form of a mist, wherein the methanol gas generation section vaporizes methanol sprayed via the nozzle to generate a methanol gas;
   a tubular section arranged on top of the methanol gas generation section and including an upper portion and a lower portion separated from each other by porous metal material capable of heat reflection, wherein an air supply unit is coupled to the upper portion and the tubular section provides a flow path for upwardly directing the methanol gas generated by the methanol gas generation section by natural convection; the tubular section also operating to mix the methanol gas with a predetermined proportion of air supplied from the air supply unit; and
   a catalyst section arranged on top of the upper portion of the tubular section for turning the methanol gas mixed with the air at the predetermined proportion in the tubular section into radicals by a catalyzed reaction,
   wherein the catalyst section is formed by stacking a plurality of turn-into-radical reaction catalyst layers, each of the plurality of catalyst layers having been obtained by forming a thin metal sheet to a honeycomb structure.

2. The device for generating a sterilizing gas according to claim 1, wherein the turn-into-radical reaction catalyst layer has a honeycomb structure obtained on forming the thin metal sheet(s) to a corrugated shape.

3. The device for generating a sterilizing gas according to claim 2, wherein the catalyst section is formed by stacking the plurality of turn-into-radical reaction catalyst layers as a phase of the corrugated shape is shifted.

4. The device for generating a sterilizing gas according to claim 1, wherein the catalyst section is exchangeable.

5. A catalyst cartridge exchangeably mounted in a device for generating a sterilizing gas; the device for generating a sterilizing gas comprising:
   a methanol gas generation section including a nozzle that sprays methanol supplied from a methanol tank in the form of a mist, wherein the methanol gas generation section vaporizes methanol sprayed via the nozzle to generate for a methanol gas; and
   a tubular section arranged on top of the methanol gas generation section and including an upper portion and a lower portion separated from each other by porous metal material capable of heat reflection, wherein an air supply unit is coupled to the upper portion and the tubular section provides a flow path for upwardly directing the methanol gas generated by the methanol gas generation section by natural convection; the tubular section also operating to mix the methanol gas with a predetermined proportion of air supplied from the air supply unit,
   wherein the catalyst cartridge is formed by stacking a plurality of turn-into-radical reaction catalyst layers, each of the plurality of catalyst layers having been obtained by forming a thin metal sheet to a honeycomb structure; the catalyst cartridge being arranged on top of the tubular section; the catalyst cartridge turning the methanol gas, mixed with a predetermined proportion of air in the tubular section, into radicals by a catalyzed reaction.

6. The catalyst cartridge according to claim 5, wherein the turn-into-radical reaction catalyst layer is of a honeycomb structure obtained on forming the thin metal sheet to a corrugated shape.

7. The catalyst cartridge according to claim 6, wherein the catalyst cartridge is formed by stacking the plurality of the turn-into-radical reaction catalyst layers as a phase of the corrugated shape is shifted.

8. A system for sterilization, the system comprising:
   a device for generating a sterilizing gas; the device for generating a sterilizing gas comprising:
      a methanol gas generation section including a nozzle that sprays methanol supplied from a methanol tank in the form of a mist, wherein the methanol gas generation section vaporizes methanol sprayed via the nozzle to generate a methanol gas;

a tubular section arranged on top of the methanol gas generation section and including an upper portion and a lower portion separated from each other by porous metal material capable of heat reflection, wherein an air supply unit is coupled to the upper portion and the tubular section provides a flow path for upwardly directing the methanol gas generated by the methanol gas generation section by natural convection; the tubular section also operating to mix the methanol gas with a predetermined proportion of air supplied from the air supply unit; and a catalyst section arranged on top of the upper portion of the tubular section for turning the methanol gas mixed with the air at the predetermined proportion in the tubular section into radicals by a catalyzed reaction, wherein the catalyst section is formed by stacking a plurality of turn-into-radical reaction catalyst layers, each of the plurality of catalyst layers having been obtained by forming a thin metal sheet to a honeycomb structure.

\* \* \* \* \*